United States Patent [19]
Dingley

[11] Patent Number: 5,277,178
[45] Date of Patent: Jan. 11, 1994

[54] MEDICO-SURGICAL DEVICE

[76] Inventor: John Dingley, Morriston Hospital, Morriston, Swansea, West Glamorgan, SA6 6NL, Wales

[21] Appl. No.: 937,041

[22] Filed: Sep. 1, 1992

[30] Foreign Application Priority Data

Sep. 14, 1991 [GB] United Kingdom ............ 9119703

[51] Int. Cl.⁵ ............................ A61M 16/00
[52] U.S. Cl. ............................ 128/200.26
[58] Field of Search .......... 128/206.29, 200.26, 128/207.13; 602/902; 604/27

[56] References Cited

U.S. PATENT DOCUMENTS

| | | | |
|---|---|---|---|
| 3,756,244 | 9/1973 | Kinnear et al. | 128/351 |
| 4,067,331 | 1/1978 | Berman | 128/208 |
| 4,211,234 | 7/1980 | Fisher | 128/200.26 |
| 4,338,930 | 7/1982 | Williams | 128/200.26 |
| 4,612,927 | 9/1986 | Kruger | 128/200.26 |
| 4,683,879 | 8/1987 | Williams | 128/200.26 |
| 4,694,826 | 9/1987 | Chester | 128/303 R |
| 4,919,126 | 4/1990 | Baildon | 128/207.14 |
| 4,982,729 | 1/1991 | Wu | 128/200.26 |
| 4,995,388 | 2/1991 | Brain | 128/207.13 |
| 5,042,469 | 8/1991 | Augustine | 128/200.26 |

FOREIGN PATENT DOCUMENTS

| | | |
|---|---|---|
| 0150465 | 8/1985 | European Pat. Off. . |
| 9209325 | 6/1992 | European Pat. Off. . |
| 3400872 | 7/1985 | Fed. Rep. of Germany ............ 128/200.26 |
| 1321406 | 6/1973 | United Kingdom . |
| 2084877 | 4/1982 | United Kingdom . |
| 2137096 | 10/1984 | United Kingdom . |

*Primary Examiner*—John G. Weiss
*Attorney, Agent, or Firm*—Pollock, VandeSande and Priddy

[57] ABSTRACT

An introducer for use in the insertion of an airway comprises a bendable plastics channel which extends from the teeth and is curved to lie against the hard palate. The introducer protects delicate tissue and guides the airway during insertion. A flange and a finger grip projects from the airway where its protrudes from the mouth.

3 Claims, 2 Drawing Sheets

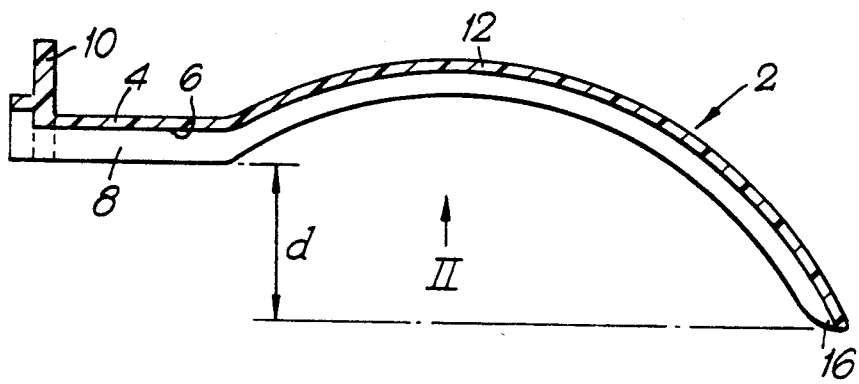
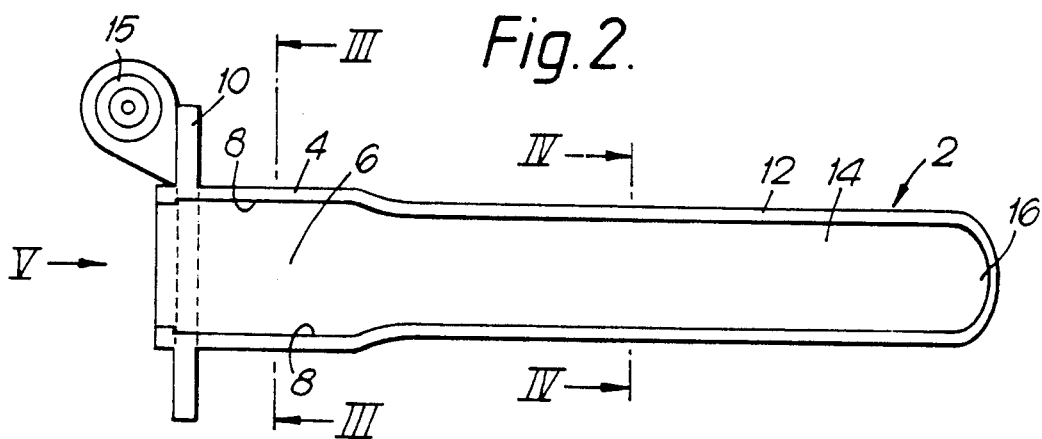
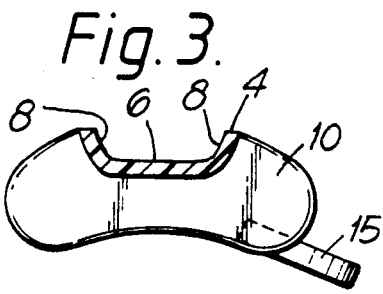
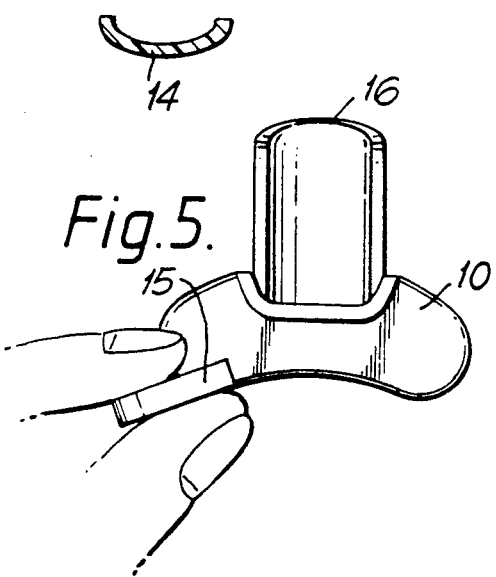

MEDICO-SURGICAL DEVICE

BACKGROUND OF THE INVENTION

This invention relates to medico-surgical devices for facilitating insertion of a tube or similar device to the pharynx.

The invention is more particularly concerned with devices for facilitating the insertion of tubes or the like into the pharynx of a patient.

It is common practice to use an airway known as a laryngeal mask for the administration of anaesthetic and ventilation gases to a patient. These airways comprise a tube with a mask or cuff at one end, the tube being inserted in the patient's mouth so that one end is located in the hypopharynx and so that the mask forms a seal in this region with the surrounding tissue. Laryngeal masks have several advantages over endotracheal tubes which are longer and seal with the trachea below the vocal folds. One problem, however, with laryngeal masks is that insertion can cause trauma to the pharyngeal wall. This is because the tip of the mask has a tendency to stick in the pharynx as a result of the sharp turn it has to negotiate before it seats itself in the hypopharynx. These problems have been reported in, for example, Anaesthesia 1989; 44: 703 by van Heerden and Kirrage. Although the risk of damage can be reduced by ensuring that the head of the patient is correctly positioned during insertion, where the anaesthetist is not completely familiar with the correct technique, there is still an associated risk of trauma. Blood is often seen on the laryngeal mask when it is removed, even when the anaesthetist is experienced in the technique.

BRIEF SUMMARY OF THE INVENTION

It is an object of the present invention to provide a device that can be used to reduce the risk of trauma caused by insertion of airways or similar devices and to increase the probability of successful insertion.

According to one aspect of the present invention there is provided a medico-surgical device for facilitating insertion of a tube or similar device to the pharynx comprising a member that is curved along a major part of its length and extends from the teeth of the patient to the region of the pharynx such that, in use, the device lies adjacent the hard palate of the mouth and protects the hard palate and pharynx from damage during insertion of the tube.

The curved member of the device is preferably of channel shape with the channel opening on the inner side of the curve such that the inner surface of the device provides a guide along which the tube can be inserted.

The device is preferably of a bendable material such as of a plastics. The device may have a flange at one end which is adapted, in use, to lie against the lips of the patient. The device may have a finger grip at the end close to the teeth.

According to another aspect of the present invention there is provided a medico-surgical assembly comprising a device of the above-specified kind and a tube lying against the inner side of the curve of the device.

An introducer for a laryngeal mask, in accordance with the present invention, will now be described, by way of example, with reference to the accompanying drawings.

BRIEF DESCRIPTION OF THE DRAWINGS

FIG. 1 is a sectional side elevation of the introducer;
FIG. 2 is a view of the introducer from below in the direction of the arrow II in FIG. 1;
FIG. 3 is a lateral section along the line III—III of FIG. 2;
FIG. 4 is a lateral section along the line IV—IV of FIG. 2;
FIG. 5 is an end view from the left along the arrow V.

DETAILED DESCRIPTION OF THE PREFERRED EMBODIMENT

Figure 6:
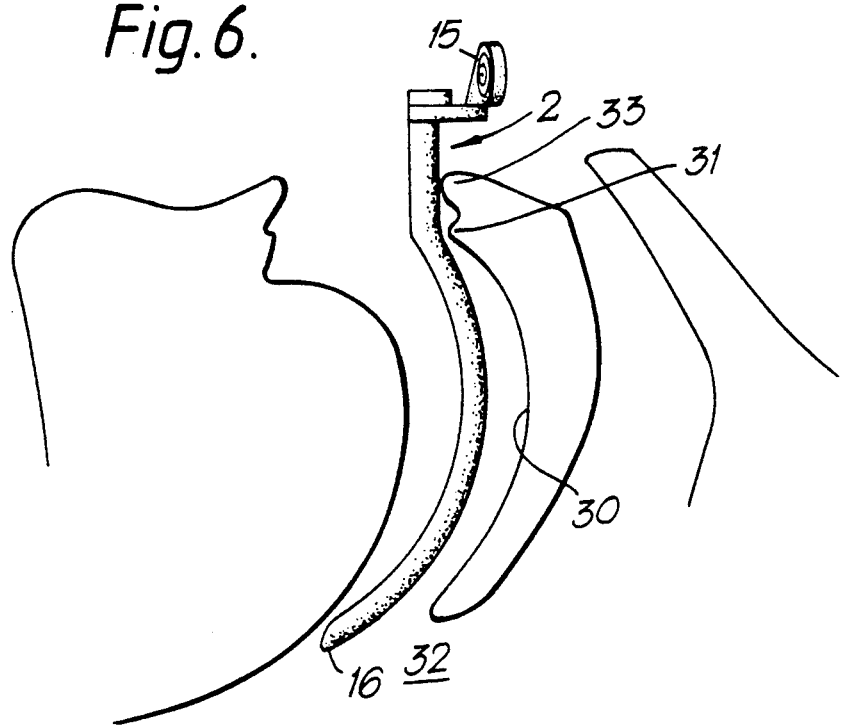
FIGS. 6 and 7 are side elevation views of the introducer in use.

With reference to FIGS. 1 to 5, the introducer 2 is a generally channel-shape, one-piece, integral moulding of a soft plastics material with a low coefficient of friction, such as PVC, with a wall thickness of about 2 mm. At its left-hand, external end, the introducer has a short portion 4 which is straight and extends for about 26 mm. The portion 4 has a flat floor 6 and shallow curved walls 8 which give the portion an external depth of about 6 mm and an external width across its open side of about 24 mm. A flange 10 projects radially around the straight portion 4 close to its left-hand end. The flange 10 is of a generally C shape with a width of about 60 mm which is sufficient, in use, to prevent insertion of the external end of the introducer into the mouth. The flange 10 has an axially-projecting finger grip 15 on one side which enables the introducer to be gripped by the finger and thumb of the left hand of the anaesthetist.

Extending from the right-hand end of the straight portion 4, the introducer has a curved portion 12 which forms the major part of the length of the introducer. The curved portion 12 is also of channel shape but, in section, has a rounded floor 14 with a depth of about 5 mm. The curved portion tapers slightly along its length, having an external width across its open side of about 18 mm towards its internal, right hand end. The direction of curvature is such that the channel opens on the inside of the curve, with the radius of curvature being about 60 mm and the circumference of the curved portion being about 95 mm, giving the introducer an overall length of about 115 mm. The center of curvature of the curved portion 12 is not located midway along the length of the curved portion but is displaced towards the left-hand end so that the right-hand, internal end of the introducer is displaced below the straight portion 4 by a distance d of about 21 mm. The right-hand end of the introducer has a smoothly-rounded tip 16.

The dimensions and shape of the introducer are selected to conform to the anatomy of the patient, as will become apparent from the description of the manner of use of the introducer. Different size introducers will be necessary with patients of different builds, such as, for example, with children.

Figure 7:
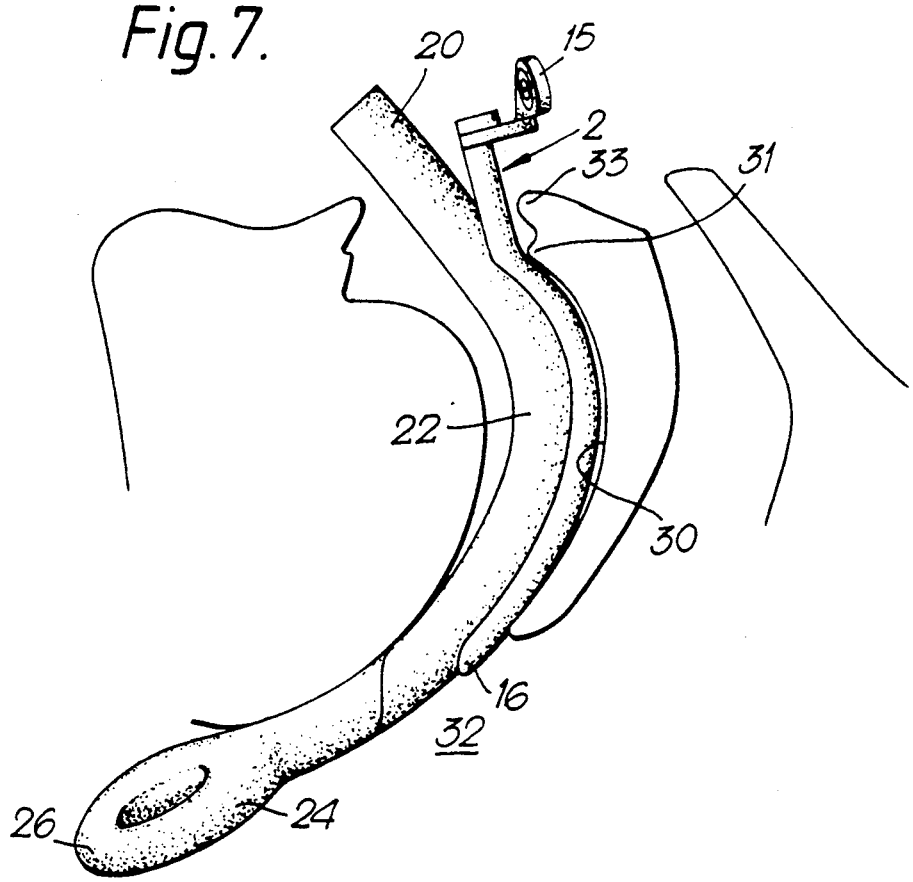

With reference now to FIGS. 5 to 7, the manner of use of the introducer will be described.

The patient is placed in the usual position for introduction of an oral tube or laryngeal mask, with his neck flexed, his head rotated back and his mouth open. The introducer is lubricated on both sides, such as with a hydrophilic gel, and is gripped by its grip 15 with the tip 16 pointing down into the patient's mouth and with the open side of the channel directed caudally. The forward or internal end of the introducer is pushed into the patient's mouth so that the convex side of the curved portion 12 slides smoothly over the hard palate 30 and pharynx 32 until the flange 10 lies against the patient's upper lip. In this position, the tip 16 lies in the region of the pharynx, as shown in FIG. 6. The soft nature of the plastics from which the introducer 2 is made, and the curved, open channel shape, give the introducer flexibility towards its forward end so that it readily conforms to the patient's anatomy as it is slid into position, without trauma. Damage to the patient's teeth during insertion is also avoided because of the flexible nature of the introducer 2. When correctly located, the introducer 2 provides a guide along which the airway 20 can be inserted.

The airway 20 is a laryngeal mask of conventional form, such as described in GB2111394A, and comprises a curved tube 22 which opens at one end into a cuff or hollow mask portion 24 that is located on one side of the tube and, in use, conforms to the space behind the larynx and seals around the circumference of the laryngeal inlet but without penetrating the larynx itself. The tubular construction of the airway 20 makes it relatively stiff so that it can maintain an open gas passage against pressure from the patient's anatomy around it. The airway 20 is inserted by placing its tip 26 against the external end of the introducer 2 in the region of the patient's lips 33, with the mask of the airway directed away from the introducer. The width of the introducer 2 is such that the tubular component of the airway 20 is received snugly within the channel of the introducer with the mask portion 24 overlapping the edges of the channel on both sides. The airway 20 is then slid along the introducer 2 which guides it to the position shown in FIG. 7. Correct positioning of the patient's head is less critical because of the guide provided by the introducer; this significantly increases the chance of successful insertion of the laryngeal mask.

Because the introducer is located between the airway and the patient's tissue, it protects the pharnyx and hard palate from the airway, thereby reducing trauma. The flexible nature of the introducer 2 enables it to mould itself to the shape of the palate and pharynx as the mask is inserted, thereby reducing localized pressure on the patient's tissue. The introducer protects the upper set of teeth 31 from damage by the airway while the flexible nature of the introducer means that it does not impede the airway at the teeth.

After insertion of the airway, the introducer 2 is pulled out, leaving the airway in position. The introducer can then be disposed of. Alternatively, the introducer could be left in situ and only removed with the airway.

Although it is preferable that the introducer is of a soft plastics or similar material such as silicone rubber, it would be possible to provide an introducer made of a metal. Such an introducer need not have a channel shape, although this is preferable, but could be flat across its width. The introducer could also be used to facilitate introduction of other tubes, or the like.

What I claim is:

1. A medico-surgical assembly comprising a laryngeal mask and a guide, the guide comprising a curved, channel-shape member of a bendable material which is open on an inner side of its curvature along its entire length, the guide having a flange at one end that in use lies against the lips of a patient, the guide extending in use from said one end to an opposite end located in the region of the patient's pharynx such that the device lies adjacent the hard palate of the patient's mouth, the laryngeal mask being slidable along the guide so that it can be slid into the region of the pharynx without damage to patient tissue protected by the guide whereafter the guide can be removed leaving the mask in place.

2. A medico-surgical device according to claim 1, wherein the device is of a plastics.

3. A medico-surgical device according to claim 1, wherein the device has a finger grip at an end close to the teeth of the patient.

* * * * *